US011286451B2

(12) United States Patent
Morgan et al.

(10) Patent No.: US 11,286,451 B2
(45) Date of Patent: Mar. 29, 2022

(54) FUNNEL-GUIDED MICROTISSUE STACKING AND MANIPULATION (71) Applicant: BROWN UNIVERSITY, Providence, RI (US)

(72) Inventors: Jeffrey R. Morgan, Sharon, MA (US); Kali L. Manning, Pawtucket, RI (US); Blanche Ip, Providence, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 16/967,182

(22) PCT Filed: Feb. 5, 2019

(86) PCT No.: PCT/US2019/016683
§ 371 (c)(1),
(2) Date: Aug. 4, 2020

(87) PCT Pub. No.: WO2019/153006
PCT Pub. Date: Aug. 8, 2019

(65) Prior Publication Data
US 2020/0377835 A1 Dec. 3, 2020

Related U.S. Application Data (60) Provisional application No. 62/626,458, filed on Feb. 5, 2018.

(51) Int. Cl.
C12M 3/00 (2006.01)
C12N 5/00 (2006.01)
C12M 3/06 (2006.01)

(52) U.S. Cl.
CPC ........... *C12M 23/16* (2013.01); *C12N 5/0068* (2013.01); *C12N 2513/00* (2013.01)

(58) Field of Classification Search
CPC ... C12M 23/16; C12N 5/0068; C12N 2513/00
See application file for complete search history.

(56) References Cited

U.S. PATENT DOCUMENTS

| | | | |
|---|---|---|---|
| 9,771,554 B2 | 9/2017 | Morgan et al. | |
| 2015/0024495 A1* | 1/2015 | Morgan | C12M 25/02 435/401 |
| 2016/0032229 A1* | 2/2016 | Egeler | B01L 3/5085 435/305.2 |
| 2019/0002834 A1* | 1/2019 | Tanabe | C12N 5/0696 |
| 2020/0208088 A1* | 7/2020 | Frey | C12M 21/08 |

OTHER PUBLICATIONS

Kim, et al., "96-Well Format-Based Microfluidic Platform for Parallel Interconnection of Multiple Multicellular Spheroids", Journal of Laboratory Automation, vol. 20, No. 3, Jun. 2015, pp. 274-282.
Manning, et al., "Funnel-Guided Positioning of Multicellular Microtissues to Build Macrotissues", Tissue Engineering: Part C, , vol. 24, No. 10, Sep. 20, 2018, pp. 557-565.
International Search Report and Written Opinion, PCT/US/016683, dated Apr. 8, 2019 25 pages.

\* cited by examiner

*Primary Examiner* — Nathan A Bowers
(74) *Attorney, Agent, or Firm* — Adler Pollock & Sheehan P.C.

(57) ABSTRACT

The invention provides a device and a method for the assembly of an aggregation of adherent cells, particularly a three-dimensional assembly of adherent cells.

7 Claims, 6 Drawing Sheets

FUNNEL-GUIDED MICROTISSUE STACKING AND MANIPULATION

CROSS REFERENCE TO RELATED APPLICATIONS

This application is a national phase filing under 35 U.S.C. § 371 of International Application No. PCT/US2019/016683 filed Feb. 5, 2019, which claims priority from U.S. Provisional Patent Application No. 62/626,458, filed Feb. 5, 2018, the entire contents of which are hereby incorporated by reference herein.

STATEMENT REGARDING FEDERALLY SPONSORED RESEARCH OR DEVELOPMENT

This invention was made with government support under grant CBET-1428092 awarded by the National Science Foundation. The government has certain rights in the invention.

FIELD OF THE INVENTION

This invention generally relates to a device for assembling and stacking aggregations of adherent cells for use in the field of tissue engineering, and more particularly to the in vitro engineering of thick tissues of high cell density. A method of using the device is also provided.

BACKGROUND OF THE INVENTION

A long-standing problem to tissue engineering is the in vitro fabrication of large tissue constructs with high densities of living cells, similar to natural organs and tissues. While there are numerous hurdles, a notable issue is that the diffusion of oxygen, nutrients, and metabolic waste products limits cellular tissues to thicknesses of 100-200 µm to maintain viability. In natural organs and tissues, a branching vascular supply ensures that all cells are close to blood vessels. Tissue engineering approaches to this problem have included efforts to make an artificial vascular tree by microfabrication of degradable polymers, the assembly of modules of cells and collagen, and the layer-by-layer printing of cells and extracellular-matrix-like materials.

To date, most successful tissue engineering applications have used thin tissues (<2 mm), in which transport of oxygen, nutrients, and metabolic waste critical for cell viability occurs by diffusion. In highly cellular tissues, this distance is thought to be 100-200 µm, challenging the tissue engineering art to design large tissue constructs that are or can become vascularized.

Bio-printers (adapted inkjet printers) were developed to try and meet the challenge of printing 3D organs, but they have had limited success. First reported in 2005, bio-printers fabricate structures by a dropwise printing of cells with an extracellular matrix (ECM) material, which serves as the "bio-glue." The bio-glue gels within minutes, but the cells require tens of hours to attach to the extracellular matrix. Recently, bio-printers have become commercially available. However, success is limited to simple structures such as a single tube or an array of spheroids. The structures survive by passive diffusion, and none even begin to approach the complexity, nor cell density of an organ. Bio-printers are also limited by slow throughput, which is inherent in the small size/simplicity of their building materials as well as the vast number of building units that must be deposited. Bio-printers deposit (one at a time) a drop of either a spheroid (˜1,000 cells) or liquid extracellular matrix. Bio-printers are currently not creating thick structures with sufficient density of cells to require perfusion. The "Kenzan" methods create structures of modest thickness, high extracellular matrix content, and low cell density that do not require perfusion. See, Moldovan et al. (2017) Tissue Eng. B Rev. 23, 237; Itoh et al. (2015) PLoS One 10, e0145971.

The aggregation of cells into the formation of large living parts that have a high cell density serves as a viable alternative to bio-printers for the formation of thick structures with sufficient density of cells to require perfusion. See, e.g., U.S. Pat. No. 8,361,781 (Morgan et al.), herein incorporated by reference in its entirety. However, current pick-and-place instruments from the electronics industry are not suitable, nor could they be easily modified to work within an aqueous environment of cell culture medium to assemble these aggregation of adherent cells to form higher ordered structures. Additionally, microbiology instruments for picking bacterial colonies are not suitable because they locate a colony and punch out a small plug of agarose and dispense this plug (with colony) to a 96 well plate. These instruments (e.g., Hudson Robotics) are designed for very high throughput, do not have the necessary precision and would certainly damage our tissues and cannot grip, let alone perfuse a growing organ.

U.S. Pat. No. 9,771,554 (Morgan et al.), herein incorporated by reference in its entirety, discloses a versatile building platform that assembles relatively large 3D tissues/organs layer-by-layer. The Bio-Pick, Place, and Perfuse (Bio-P3) building platform uses a controllable low-level suction head to pick up living microtissue building parts and place them onto other microtissue building parts in precise locations while maintaining perfusion as these parts fuse and the living structure is built. This building platform can grip multi-cellular building parts of any size, shape and cell type.

The ability to build organs in vitro has a far-reaching impact in the tissue engineering art, as well as in many other areas of research that use animals. Many of these programs have an unmet need to create new more complex 3D in vitro models (test beds) that more accurately mimic the complexity of in vivo. However, there remains a continuing need for new and simplified devices and methods that can be used to construct complex three-dimensional test beds of tissues of specified shape and size.

SUMMARY OF THE INVENTION

The invention provides a funnel-guide device and method for the assembly of an aggregation of adherent cells. The invention also provides three-dimensional assemblies of adherent cells. The funnel-guide device and method of the invention can be used to build macrotissues layer-by-layer. The funnel-guide device and method of the invention provide an additive manufacturing strategy for the non-contact manipulation and positioning of multi-cellular microtissues. The funnel-guide technology is both a principle for the manipulation of microtissues and a platform for the layer-by-layer positioning of microtissue building blocks to form macrotissues.

In a first embodiment, the invention provides a device, a funnel-guided tissue fabrication instrument, for assembling multi-cellular structures. The device comprises a funnel-guide. The funnel-guide comprises (a) optionally, a free fall chamber, (b) a funnel chamber, and (c) a stacking chamber.

Figure 3:
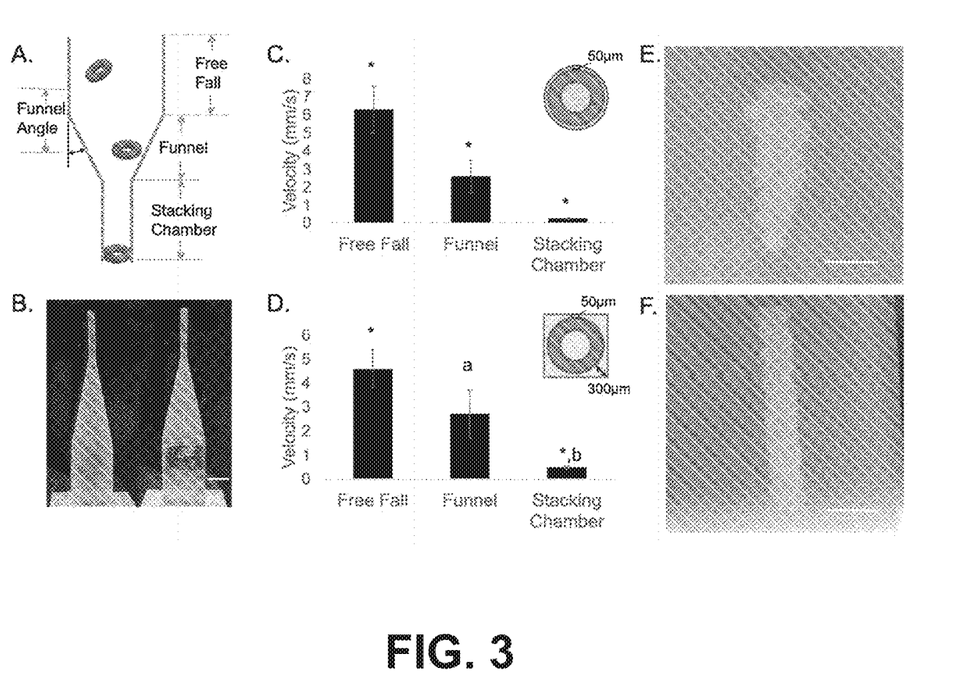
FIG. 3 is a set of figures, images, and charts showing the design and testing of the funnel-guide (FG).
Figure 4:
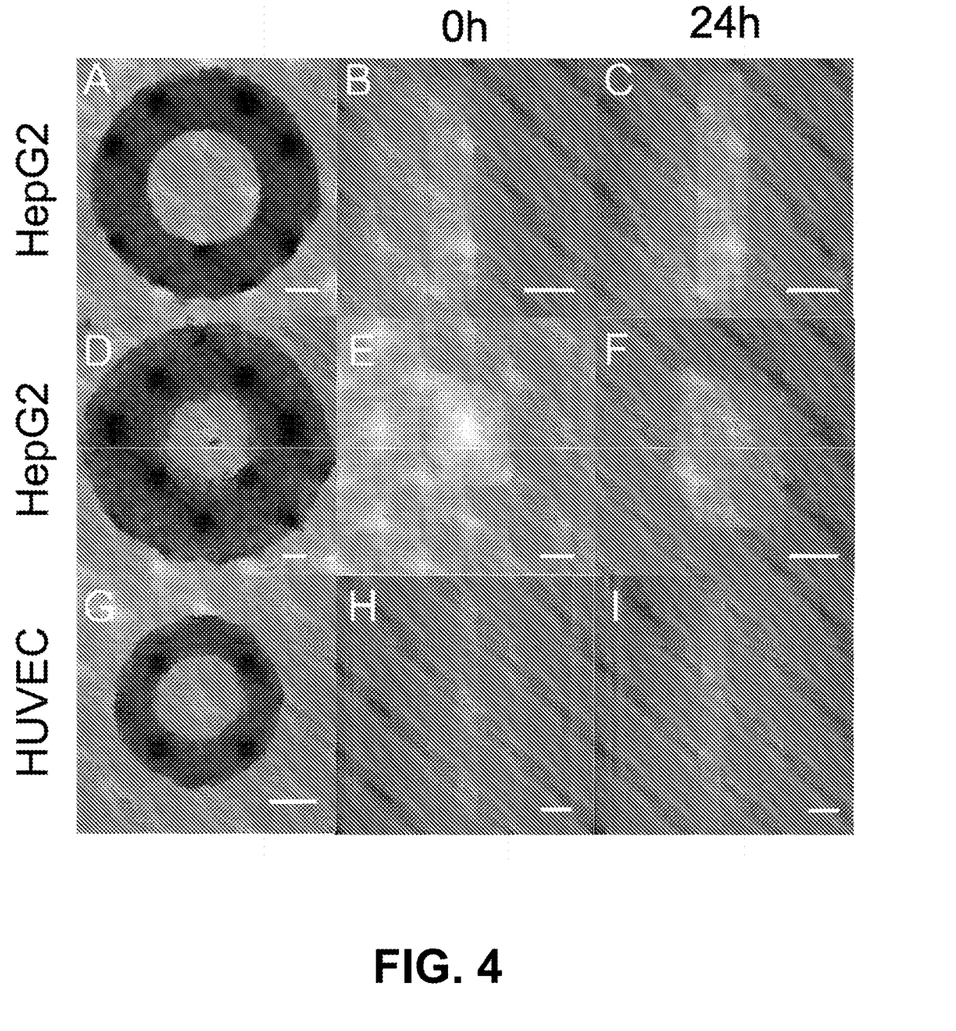
FIG. 4 is a set of images showing that funnel-guides can stack larger toroids and toroids of different cell types.

In a second embodiment, the funnel-guide device has a Y-shape funnel. An example of a funnel-guide device having a Y-shape funnel is shown in FIG. 3A. In a third embodiment, the funnel chamber has a funnel angle (∡) that is greater than 30° but is less than 90°, including any value or range therebetween. An example of a funnel-guide device having a funnel angle is shown in FIG. 3A. In a fourth embodiment, the funnel chamber has a funnel angle (∡) that is greater than 35° but is less than 85° including any value or range therebetween. In a fifth embodiment, the funnel chamber has a funnel angle (∡) that is greater than 40° but is less than 85° including any value or range therebetween. In a sixth embodiment, the funnel chamber has a funnel angle (∡) that is greater 45° but is less than 85° including any value or range therebetween. In a seventh embodiment, the funnel chamber has a funnel angle (∡) that is greater than 50° but is less than 80°, including any value or range therebetween. In an eighth embodiment, the funnel chamber (∡) has a funnel angle that is 77°.

In a ninth embodiment, the funnel chamber has an angle of from 30°≤ ∡ ≤77° (i.e., greater than or equal to 30° and less than or equal to 77°).

The free fall chamber of the funnel-guide can vary in height determined by the specific needs of the user. In a tenth embodiment, the free fall chamber is at least 10 mm in height. In an eleventh embodiment, the free fall chamber has a 10 mm free-fall space.

The stacking chamber can have various shapes, and the shape design of the stacking chamber can depend on the shape of the multi-cellular structures being stacked. In a twelfth embodiment, for stacking toroids, the funnel and stacking chamber sections are square-shaped. Using a square shape for the stacking chamber decreases the resistance between the microtissue multi-cellular structures and the mold wall of the stacking chamber. The use of square-shaped stacking chamber having a 300 µm space on the four corners and about a 50 µm gap along the sides resulted in an aligned stack of toroids. In a thirteenth embodiment, for stacking toroids, the funnel and stacking chamber sections are octagon-shaped. In a fourteenth embodiment, for stacking honeycomb shaped multi-cellular structures, the stacking chamber section is a honeycomb-shaped stacking chamber. The use of a honeycomb-shaped stacking chamber having about a 50 µm gap around the sides of each lumen of the honeycomb-shaped multi-cellular structures resulted in an aligned stack of honeycomb-shaped structures within the stacking chamber.

In a fifteenth embodiment, the device comprises a stacking chamber with a diameter slightly larger than the diameter of the toroid or honeycomb-shaped single multi-cellular structures described herein. In a sixteenth embodiment, the funnel-guide comprises a 10 mm free-fall space for the toroid to right itself, a funnel with an angle between 30°≤ ∡ ≤77°, and a stacking chamber with a diameter slightly larger than the diameter of the toroid or honeycomb-shaped single multi-cellular structures described herein.

The inventors used agarose micro-molds to self-assemble cells into toroid-shaped and honeycomb-shaped microtissues and observed that when falling in the cell culture medium, the microtissues spontaneously righted themselves to a horizontal orientation.

In a seventeenth embodiment, the funnel-guided device of the invention further comprises a vision recognition to identify small multi-cellular structures, such as the toroid or honeycomb-shaped single multi-cellular structures described herein.

In an eighteenth embodiment, the funnel-guided tissue device of the invention further comprises a pipette that can be used to retrieve and remove the assembled stacked multi-cellular structures from a mold or a vessel, and then transfer and deposit the assembled multi-cellular structures to a second vessel containing a funnel-guide. Alternatively, the pipette can be used to retrieve and remove a single toroid from the mold. In a nineteenth embodiment, the pipette is an automated pipette.

In a twentieth embodiment, the invention provides a method for assembling multi-cellular structures. The method comprises the step of depositing a multi-cellular structure to a funnel-guide. The funnel-guide comprises (a) optionally, a free fall chamber, (b) a funnel chamber, and (c) a stacking chamber. As the data disclosed herein demonstrate, after a single multi-cellular structure, such as a toroid or honeycomb-shaped single multi-cellular structures described herein, is transferred to the funnel-guide, the multi-cellular structures slowly settle in the liquid. The design of the funnel-guide device allows them to settle into desired positions within the funnel stack of the funnel.

In a twenty-first embodiment, the small multi-cellular structures vertically align within the stacking chamber. The method of use comprises the transfer of a single multi-cellular structure to the funnel-guide. This step is then repeated to build a stack of single multi-cellular structure within the stacking chamber of the funnel-guide until a suitable number of aggregations of cells (single multi-cellular structures) have been assembled to form a large, stacked multi-cellular structure. The number of single multi-cellular structures assembled within the stacking chamber is indefinite and only limited by the size of the stacking chamber.

The method of the invention is a method of microtissue manipulation, providing for the precise placement of living structures into assemblies of parts that fuse to form larger living structures. Accordingly, in a twenty-second embodiment, the invention provides single multi-cellular structures that are vertically aligned within the stacking chamber. In a twenty-third embodiment, the large, stacked multi-cellular structure comprises a tube, such as a small diameter blood vessel. In a twenty-fourth embodiment, the number that defines a stack is two, such as for an artificial cornea.

In a twenty-fifth embodiment, the large stacked multi-cellular structure within the stacking chamber is an aligned stack of toroids. As shown by the data disclosed herein, the use of square-shaped stacking chamber having a 300 µm space on the four corners and about a 50 µm gap along the sides resulted in an aligned stack of toroids.

In a twenty-sixth embodiment, the method of the invention further comprises a vision recognition step of identifying small multi-cellular structures, such as the toroid or honeycomb-shaped single multi-cellular structures described herein. In this embodiment, one of skill in the tissue engineering art visualizes the multi-cellular structures in the funnel guide. In a twenty-seventh embodiment, the method also provides a QC/QA step, namely watching that the single multi-cellular structure parts before or when they are added to the funnel guide and then settle correctly and align correctly to form the assembled, large, stacked multi-cellular structures, and optionally form a tube.

In a twenty-eighth embodiment, the method of the invention further comprises retrieving and removing the assembled, large, stacked multi-cellular structures from the funnel guide. The step of retrieving and removing can be performed using a pipette. Alternatively, the step of retrieving the stacked, built tubes can be performed by slicing open the funnel guide, as described in EXAMPLE 1, below. As another alternative, designed and pre-sliced funnel guides can be disassembled.

In a twenty-ninth embodiment, the method of the invention further comprises the steps of transferring and depositing the multi-cellular structures to a second vessel containing a funnel-guide.

In a thirtieth embodiment, the method of the invention comprises the steps of transferring and depositing the multi-cellular structures to a second vessel containing a funnel-guide.

In a thirty-first embodiment, the invention provides a method of building a liver, such a liver for humans. The human liver has about 240 billion cells. Bianconi et al. *Annals of Human Biology*, 40, 463-471 (2013). The volume of the liver is ~2 liters. Heinemann et al., *Liver Transplantation and Surgery* 5: 366-368 (1999). A honeycomb part may have close to 10 million cells, so to build a liver would require picking and placing about 24,000 parts of this size. Larger parts would mean fewer stacks.

In a thirty-second embodiment, the invention provides a method of building a "mega" organ, not for transplantation, but rather for the in vitro synthesis and secretion of valuable biomedical products, such as recombinant proteins. These human-made mega organs are like bio-manufacturing facilities, and so have even more stacks.

The invention provides three-dimensional assemblies of adherent cells, which are large, stacked multi-cellular structures. In a thirty-third embodiment, the invention provides an aligned stack of toroids. In a thirty-fourth embodiment, the invention provides an aligned stack of honeycomb-shaped structures. In a thirty-fifth embodiment, the invention provides an aligned stack of living building parts containing a lumen, for a tube built from a stack of toroids. For a stack of honeycombs with multiple holes, the built structure contains lumina.

In a thirty-sixth embodiment, the three-dimensional assemblies of adherent cells provide for the perfusion or pumping of fluid through the stacked multi-cellular structures. This fluid is cell culture medium containing the nutrients needed to keep the built structure alive and well after it is built.

BRIEF DESCRIPTION OF THE DRAWINGS

The foregoing is apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A and FIG. 1B are figures showing microtissues self-assembled by seeding HepG2 cells in either toroid ($5.0\times10^4$) (FIG. 1A) or honeycomb-shaped ($3.75\times10^5$) (FIG. 1B) agarose micro-molds. FIG. 1C is a chart showing that toroid and honeycomb microtissues removed from the micro-molds slid down a 10 mm incline of 15°, 20°, and 30° and the velocity of sliding measured. FIG. 1D is a chart showing that the velocities for toroids (white bars) and honeycombs (black bars) were significantly different, and significantly different at the angles tested (p<0.0001). Values with a letter are significantly different from values with a symbol (toroid vs. honeycomb). Values with different symbols are significantly different from one another (angles tested). Values with different letters are significant from one another (angles tested). White bars represent toroids, and black bars represent honeycombs. The error bars represent standard deviation (n=30). The scale bars are 200 µm and 500 µm.

FIG. 2A, FIG. 2B and FIG. 2C are figures that show the schematics of a device with a funnel chamber and a stacking chamber designed to determine if sliding could be used to create a stack of toroids. The inventors formed the device by inserting a mold into a cuvette filled with molten agarose, then removing the mold upon solidification. The molded agarose gel was filled with media, and HepG2 toroids dropped into the funnel. FIG. 2D is an image showing dropped toroids that have settled onto the funnel wall and slid down into the stacking chamber in a vertical orientation. The scale bar is 1.5 mm. Falling toroids righted themselves to a horizontal orientation in free fall. FIG. 2E is a pair of images of spheroids (top) and toroids (bottom) falling in a cuvette filled with culture media, indicated by arrows. The toroids righted themselves to a horizontal orientation within 10 mm of free fall, as shown in the bottom right image. The scale bar is 6 mm. FIG. 2F is a chart showing the quantification of free fall velocities of HepG2 and HUVEC spheroids and toroids. HUVEC spheroid and HepG2 spheroid velocities were significantly different, and spheroid and toroid velocity values were statistically significant with a p-value <0.05 calculated by Kruskal-Wallis ANOVA on ranks, and a post hoc analysis using Dunn's Method. The error bars represent the standard deviation (n=31, 48, 37, 30 for HUVEC spheroid, HepG2 spheroid, HUVEC toroid, and HepG2 toroid respectively).

FIG. 3A is a schematic of the elements of the funnel-guide: a 10 mm free-fall space for the toroid to right itself, a funnel with an angle between $30<\measuredangle<77$, and a stacking chamber with a diameter slightly larger than the toroid diameter. FIG. 3B is a pair of images of the 3D printed molds used to mold the funnel-guide, including molds that form a circular (left) or square (right) stacking chamber. The scale bar is 5 mm. FIG. 3C is a chart showing the velocities of toroids in the free fall chamber, the funnel chamber and the stacking chamber for funnel-guides with a circular stacking chamber. FIG. 3D is a chart showing the velocities of toroids in the free fall chamber, the funnel chamber and the stacking chamber for funnel-guides with a square stacking chamber. Each value was statistically significant, with a p-value <0.05 calculated by Kruskal-Wallis ANOVA on ranks, and a post hoc analysis using Dunn's Method (n=10, circular, n=10 square). FIG. 3E is an image of a stack of toroids in the circular stacking chamber (10 HepG2 toroids). FIG. 3F is an image of a stack of toroids in the square stacking chamber (45 HepG2 toroids). The scale bars are 1 mm and 2 mm, respectively.

FIG. 4A is an image of a small HepG2 toroid ($5.0\times10^4$ cells). FIG. 4D is an image of a large HepG2 toroid ($1.2\times10^5$ cells). FIG. 4G is an image of a small HUVEC toroid ($5.0\times10^4$ cells) (FIG. 4G). The scale bars are 200 µm. FIG. 4B, FIG. 4E and FIG. 4H are images of a small HepG2 toroid, a large HepG2 toroid, and a small HUVEC toroid, correspondingly, immediately after stack formation. FIG. 4C, FIG. 4F and FIG. 4I are images of a small HepG2 toroid, a large HepG2 toroid, and a small HUVEC toroid, correspondingly, twenty-four hours after incubation at 37° C. FIG. 4B and FIG. 4C show a stack of forty small HepG2 toroids. The scale bars are 1.5 mm. FIG. 4E and FIG. 4F show a stack of twenty large HepG2 toroids. The scale bars are 1.0 mm. FIG. 4H and FIG. 4I show a stack of twenty-five small HUVEC toroids. The scale bars are 1.0 mm.

FIG. 5A is an image of a honeycomb microtissue formed by seeding HepG2 cells ($3.75 \times 10^5$ cells) into an agarose micro-mold. The scale bar is 500 µm. FIG. 5B is a pair of images of honeycombs (arrows) in free fall in a cuvette righting themselves to a horizontal orientation. The scale bar is 6 mm. FIG. 5C is a cross section diagram of funnel-guide with a honeycomb-shaped stacking chamber 3.5 mm in maximum diameter. FIG. 5D is a pair of side view images of a stack of ten HepG2 honeycombs formed by a funnel-guide designed for honeycombs, both immediately after stack formation (left) and twenty-four hours after incubation at 37° C. (right). The scale bars are 2 mm. The velocities for honeycombs (±standard deviation) in the free fall chamber (6.9±1.9 mm/s), the funnel chamber (3.0±0.4 mm/s) and the stacking chamber (0.44±0.08 mm/s) were statistically significant with a p-value <0.05 calculated by Kruskal-Wallis ANOVA on ranks, and a post hoc analysis using Dunn's Method (n=20). FIG. 5E is an image from below of a stack of five HepG2 honeycombs showing the alignment of lumens. The scale bar is 500 µm.

In FIG. 6A, toroids inside a pipette tip are imaged looking into the pipette from the bottom using a proprietary imaging system. A LabVIEW algorithm that finds circular edges is used to identify the inner pipette edge (light blue circle), then the outer edge of the toroid (red circle), and then the inner edge of the toroid (dark blue line) (B). The scale bar is 1 mm.

INDUSTRIAL APPLICABILITY

The Funnel-Guided Tissue Fabrication instrument of the invention has various commercially important applications in several fields including tissue engineering (e.g., that can be used in transplantation), in vitro models, drug testing, and drug discovery. The instrument can be applied to the manipulation of microtissues, organoids, embryoid bodies, and zebrafish embryos. Each of these microtissues, organoids, embryoid bodies, and zebrafish embryos is currently being used in drug discovery and toxicity testing programs in academic labs and pharmaceutical companies. For example, in the fields of drug discovery and toxicity testing, the Funnel-Guided Tissue Fabrication instrument can be used for the precise placement of these living structures into multi-well plates (e.g., but not limited to, 96-well plates and 384-well plates) for high throughput biochemical and microscopy analyses.

DETAILED DESCRIPTION OF THE INVENTION

Definitions

"HepG2" is an immortal cell line which was derived from the liver tissue of a 15-year-old white American male with a well-differentiated hepatocellular carcinoma. These cells are epithelial in morphology, have a modal chromosome number of 55, and are not tumorigenic in nude mice. Those of skill in the tissue engineering art consider HepG2 cells to be a suitable in vitro model system for the study of polarized human hepatocytes. See, e.g., Mersch-Sundermann et al. (2004) Toxicology. 198 (1-3): 329-340. Hep G2 cells are commercially available from the American Type Culture Collection (Manassas, Va., USA) (ATCC® HB-8065™) and from Millipore Sigma (St. Louis, Mo., USA).

"High cell density," as that term is defined in U.S. Pat. No. 9,771,554 (Morgan et al.), means at least about $10^8$ cells/ml. An example of tissue having "high cell density" is the human liver. The number of cells in the human liver is estimated to be "240 billion. Bianconi et al. (2013) Annals of Human Biology, 40, 463-471, The volume of the liver, which needs to be estimated for purposes of partial hepatectomy, is "2 liters. (Heinemann et al., Standard Liver Volume in the Caucasian Population. *Liver Transplantation and Surgery* 5: 366-368, 1999). Thus, cell density in a real liver is $10^8$ cells/ml.

Figure 1:
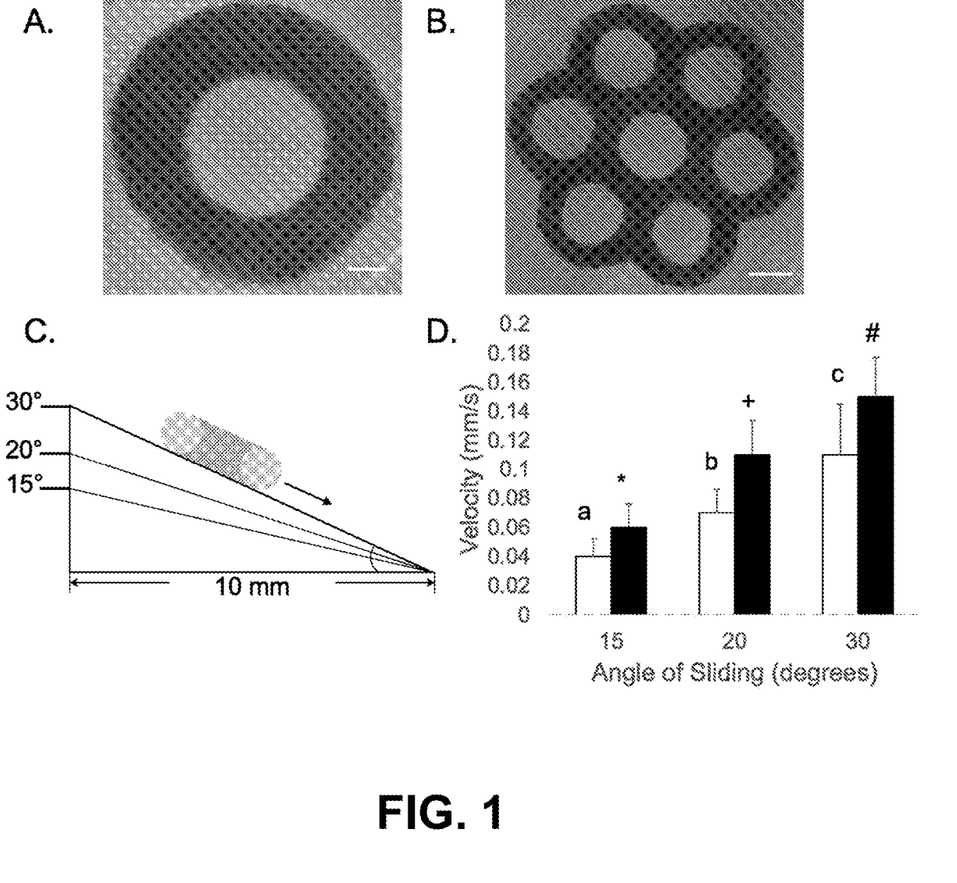
FIG. 1 is a set of figures and charts showing that the velocity of microtissue sliding depends on the angle.
Figure 5:
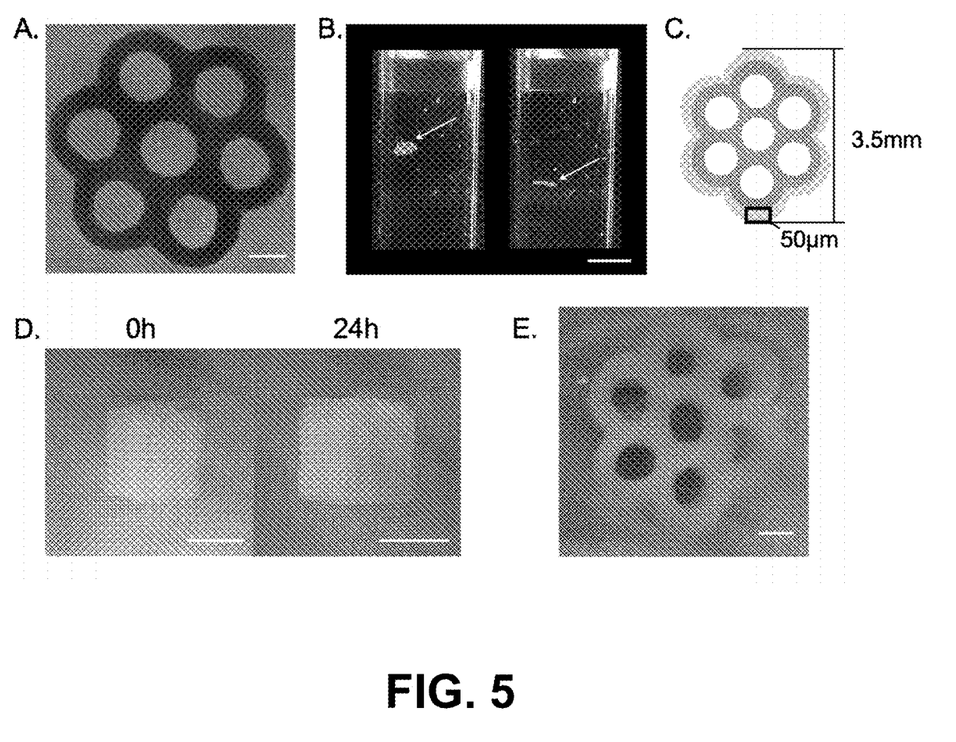
FIG. 5 is a set of figures and images showing that a funnel-guide can stack honeycombs.

"Honeycomb" shaped single multi-cellular structures are microtissues in three-dimensional cell culture. An example of a honeycomb-shaped single multi-cellular structure is shown in FIGS. 1B and 1n FIG. 5A. A single honeycomb building part can have $6 \times 10^6$ cells, equivalent to 6,000 spheroids. Dean et al. (2007) FASEB J., 21(14): 4005-12, using micro-molded, nonadhesive agarose hydrogels seeded with rat hepatoma (H35s), human fibroblasts (NHFs), or their mix (1:1), showed that cells could self-assemble rods, tori, and honeycombs. H35s cells formed intact tori and fully intact honeycombs structures with lumens even when released from the mold.

"HUVEC" cells are human umbilical vein endothelial cells derived from the endothelium of veins from the umbilical cord. Those of skill in the tissue engineering art consider HUVEC cells as a laboratory model system for the study of the function and pathology of endothelial cells (e.g., angiogenesis). See, e.g., Park et al. (2006) Stem Cell Rev. 2 (2): 93-102. Primary Umbilical Vein Endothelial Cells (Normal, Human) are commercially available from the American Type Culture Collection (Manassas, Va., USA).

"Lumen" (plural lumina) is the inside space of a tubular structure, such as an artery or intestine. The term comes from Latin lumen, meaning 'an opening.' In the biological arts, the term can refer to The interior of a vessel, such as the central space in an artery or vein through which blood flows.

"Microtissues" are cells living in 3D cell cultures cell-cell and cell-matrix interactions and complex transport dynamics for nutrients and cells.

"QC/QA" is the combination of quality assurance, the process or set of processes used to measure and assure the quality of a product, and quality control, the process of ensuring products and services meet consumer expectations. Quality assurance is process oriented and focuses on defect prevention, while quality control is product oriented and focuses on defect identification. See, Dictionary of Business Terms, Jack P. Friedman, ed. (Barron's Educational Series, 2000).

"Single multi-cellular structure" means a microtissue that can be stacked to form a large, stacked multi-cellular structure. The single multi-cellular structure can be a toroid. Alternatively, the single multi-cellular structure can be honeycomb-shaped. Other shapes of single multi-cellular structure that allows for the diffusive transport of oxygen, nutrients, and metabolic waste critical for cell viability will be known to those of skill in the tissue engineering art.

"Stacked multi-cellular structure" is a three-dimensional assembly of cells larger than single multi-cellular structures and comprising multiple single multi-cellular structures that are joined by cell-driven self-assembly.

"Standard 96-well tray" microplate is a flat plate with multiple "wells" used as small test tubes. A microplate is a standard tool in the tissue engineering art for analytical research and clinical diagnostic testing laboratories. Robots have been developed specifically to handle microplates for high-throughput assays. Ultra-low attachment (ULA) plates that support 3D cell culture are commercially available, e.g., from Thermo Fisher Scientific, Waltham, Mass., USA.

"Standard 384-well tray" microplate is a flat plate with multiple "wells" used as small test tubes. A microplate is a standard tool in the tissue engineering art for analytical research and clinical diagnostic testing laboratories. Robots have been developed specifically handle microplates for high-throughput assays. Ultra-low attachment (ULA) plates that support 3D cell culture are commercially available, e.g., from Thermo Fisher Scientific, Waltham, Mass., USA.

"Thick tissue," as that term is defined in U.S. Pat. No. 9,771,554 (Morgan et al.), means tissues that are greater in thickness than 200 microns.

"Toroid" single multi-cellular structures are microtissues in three-dimensional cell culture, a type of three-dimensional cell modeling, alternative in shape to spheroids, being formed in the shape of a torus/ring shape. An example of toroid single multi-cellular structure is shown in FIG. 1A. Dean et al. (2007) *FASEB J.,* 21(14): 4005-12, using micromolded, nonadhesive agarose hydrogels seeded with rat hepatoma (H35s), human fibroblasts (NHFs), or their mix (1:1), showed that cells could self-assemble to form rods, tori, and honeycombs. H35s cells formed intact tori and fully intact honeycombs structures with lumens even when released from the mold.

EMBODIMENTS

The invention provides a funnel-guided tissue fabrication instrument and method of use for the easy and rapid manipulation and placement of living multi-cellular structures of various sizes and shapes such as organoids, embryoid bodies, zebrafish embryos, and multi-cellular microtissues that have been self-assembled into prescribed shapes for building larger tissues (e.g., toroid, honeycomb). The funnel-guided tissue fabrication instrument and method of use do not rely on bio-inks that might be toxic and must be washed out of a construct. Additionally, the funnel-guided tissue fabrication instrument and method of use can use large living parts that have a very high cell density as single multi-cellular structures.

The living parts, which are aggregations of cells (a single multi-cellular structure) formed by cell-driven self-assembly and that are suitable for use in by the device and in the method of the invention, can be formed by a method known in the art, such as is described, e.g., in U.S. Pat. No. 8,361,781 (Morgan et al.), the entire teachings of which are incorporated herein by reference. The single multi-cellular structures that include a lumen, e.g., but not limited to the shape of a toroid or honeycomb, can be stacked to align the lumens of these parts that form channels to enable perfusion of the organ under construction by cell-driven self-assembly.

Virtually any type of cells can be used by the funnel-guided tissue fabrication instrument of the invention and method of use. There are no particular limitations concerning the cells that may be employed, as long as the cells can aggregate. The cells may be prokaryotic or eukaryotic. Any mammalian cells, e.g., mice, rat, primate (especially human), chicken, porcine, bovine, equine cells, may be used. Either primary cultured cells, an established cell line or combinations thereof can be employed. The primary cultured cells may originate from any tissue, e.g., cartilage, bone, skin, nerve, oral alimentary canal, liver, pancreas, kidney, gland, heart, muscle, tendon, fat, connective, reproductive organ tissue, ocular, blood vessel, bone marrow, and blood. Exemplary cell types include, but are not limited to, osteoblasts, keratinocytes, melanocytes, hepatocytes, gliacytes, pancreatic beta cells, pancreatic exocrine cells, neural stem cells, neural precursor cells, spinal cord precursor cells, nerve cells, mammary gland cells, salivary gland cells, renal glomerular endothelial cells, tubular epithelial cells, adrenocortical and adrenomedullary cells, cardiomyocytes, chondrocytes, skeletal and smooth muscle cells, fat and fat precursor cells, corneal and crystalline lens cells, embryonic retina cells, vascular cells, endothelial cells, bone marrow stromal cells, lymphocytes, and combinations thereof. Established cell lines include, but are not limited to, MCF-7 cells, KGN cells, HEK cells, 3T3 fibroblasts, HepG2 cells, HepG2C3A cells, H35 cells, NHF cells, HUVEC cells, and various combinations thereof. For example, the funnel-guided tissue fabrication instrument of the invention and method of use of the invention can be used to aggregate muscle cells (smooth, skeletal, cardiac), connective tissue cells (fibroblasts, monocytes, mast cells, granulocytes, plasma cells, osteoclasts, osteoblasts, osteocytes, chondrocytes), epithelial cells (from skin, gastrointestinal, urinary tract or reproductive tract, or organ epithelial cells from the liver, pancreas or spleen), or nervous system cells (glial, neuronal, astrocytes). A specific example includes the formation of blood vessels, which include the combination of smooth muscle cells and endothelial cells.

Following the assembly of a suitable number of layers of single multi-cellular structures to form a large, stacked multi-cellular structure, the assembly can be removed from the funnel-guide for suitable use. Alternatively, the multi-cellular structure can remain within vessel and perfused by perfusate that is conducted through assembly of more small multi-cellular structures, such as through openings (e.g., lumens) defined by the multi-cellular structures, thereby providing sufficient nutrients to maintain the multi-cellular structures for a period of time sufficient to cause the assembly of multi-cellular structures to fuse. The fused assembly of multi-cellular structures can then be removed from the funnel-guide for subsequent processing and use, such as for surgical use as tissue.

In a thirty-seventh embodiment, the multi-cellular structures are stacked in a manner to cause openings defined by the multi-cellular structures to substantially align. In a thirty-eighth embodiment, the multi-cellular structures are stacked in a manner that does not cause the openings defined by each multi-cellular structure to be aligned. In a thirty-ninth embodiment, different shapes of single multi-cellular structures are assembled to thereby cause formation of a large, stacked multi-cellular structure that assumes a three-dimensional character, such as that of a frustum, pyramid, or other three-dimensional shape that, upon fusion of the layers of multi-cellular structures assembled, will form a unitary three-dimensional tissue suitable for use as, for example, replacement tissue of a body part. The data disclosed herein demonstrate that once in the funnel, the multi-cellular structures slowly settle in the liquid and the precise design of the funnel-guides them into desired positions within the funnel stack of the funnel. In a fortieth embodiment, the multi-cellular structures are vertically aligned, and the lumens of the multi-cellular structures are vertically aligned, within the funnel stack of the funnel. Thus, the funnel-guided tissue fabrication instrument and method of use can be used to form any biologically relevant tube, such as blood vessels, lymph vessels, kidney tubes, bile duct tubes, and gastrointestinal (GI) tract tubes.

The following examples are given by way of illustration and are in no way intended to limit the scope of the present invention.

Examples

Example 1

Materials and Methods

Cell Culture, Micro-Mold Fabrication, and Formation of Microtissues (Single Multi-Cellular Structures).

Human hepatocellular carcinoma (HepG2) cells were expanded in Eagle's Minimum Essential Medium (EMEM) (Corning Incorporated, Corning, N.Y., USA) supplemented with 10% fetal bovine serum (FBS) (Thermo Fisher Scientific, Waltham, Mass., USA) and 1% penicillin/streptomycin (MP Biomedicals, LLC, Santa Ana, Calif., USA). Human umbilical vein endothelial cells (HUVEC) were expanded in Endothelial Growth Medium (EGM) with Supplement Kit (PromoCell, Heidelberg, Germany) and 1% penicillin/streptomycin (MP Biomedicals, LLC). Cultures were maintained in a 37° C., 5% $CO_2$ atmosphere. Cells were trypsinized, counted, and re-suspended to the desired cell density for each experiment.

The inventors cast agarose gels from 3D Petri Dish micro-molds (Microtissues, Inc., Providence, R.I., USA) as previously described by Napolitano et al. (2007) Biotechniques 43(4):494, 496-500. Agarose gels were made with powdered agarose (Low-EEO/Multi-Purpose/Molecular Biology Grade, Fisher BioReagents, Thermo Fisher Scientific) sterilized by autoclaving and then dissolved in sterile water to 2% (weight/volume). Micro-molds with different recess geometries were used to create spheroid, toroid or honeycomb microtissues. Round recesses for spheroids were 800 µm in diameter and contained 35 recesses per gel. Toroid recesses were 1400 µm in diameter with a central agarose peg of 600 µm and surrounding 400 µm trough and contained 36 recesses per gel. Large toroid recesses were 2.2 mm in diameter with a central agarose peg of 1 mm and surrounding 600 µm troughs and contained 25 recesses. The large toroid mold was a thermowax mold produced with a rapid prototyping machine (3D Systems Corporation, Andover, Mass., USA). The wax molds were used to cast 13% polyacrylamide (Dow Corning Corporation, Midland, Mich., USA) gels. Agarose gels were cast from the polyacrylamide gels.

Honeycomb recesses had a maximum diameter of 3.4 mm with a central peg and single orbital of six pegs 600 µm in diameter and a surrounding trough of 400 µm. Each gel contained a single honeycomb recess. Gels were seeded at a density of 2,000 cells per spheroid feature, 50,000 cells per toroid feature, 120,000 cells per large toroid feature, and 375,000 cells per honeycomb feature. Cells aggregated in the micro-molds, and self-assembled microtissues were used 24 hours after cell seeding.

Alternatively, one of skill in the tissue engineering art could use computer-assisted design (e.g., Solid Works, Concord, Mass.) to create a template of the desired gel features (e.g., a cell seeding chamber, 822 recesses with hemispherical bottoms (800 µm deep×400 µm wide), and media exchange ports). Then, one can generate a wax mold with a prototyping machine (e.g., a ThermoJet rapid prototyping machine), which is then used to generate a negative replicate (e.g., composed of Reprorubber, a fast-curing polydimethylsiloxane (PDMS) elastomer (Flexbar, Islandia, N.Y.)). Next, one can fill the negatives (e.g., with Sylgard 184 PDMS (Dow Corning, Midland, Mich.)) to produce positive replicates. The positive replicates are washed (e.g., with 70% ethanol, then rinsed with distilled water) and autoclaved before use. Then, one of ordinary skill in the tissue engineering can cast agarose gel bioreactors directly from wax molds, e.g., according to the methods of Napolitano et al. (2007) Biotechniques 43(4):494, 496-500, whereby aliquots of 2 g UltraPure Agarose (American Bioanalytical, Natick, Mass.) are autoclaved as a powder, then 200 mL of sterile $dH_2O$ are added and the agarose dissolved by heating and mixing on a hot plate. The solution is then cooled and approximately 2.75 mL pipetted into each wax mold in a sterile dish.

Fabrication and Use of the Funnel-Guide.

A negative replica of the funnel-guide (FG) was designed in SolidWorks (Dassault Systemes SolidWorks Corporation, Waltham, Mass., USA) and consisted of three chambers; a free fall chamber, a funnel chamber and a stacking chamber. The free fall chamber was 8 mm×8 mm and 10 mm in height, the funnel was 77°, and 13 mm in height and the stacking chamber was square-shaped, 10 mm in height and either 1.5 mm, 800 µm or 2.3 mm in diameter for the regular, small and large toroids, respectively. The funnel-guide for honeycombs had a 14 mm free fall, 77° funnel and a 3.5 mm honeycomb shaped stacking chamber. The negative replicas of the funnel-guides (FG molds) were fabricated using a Form 1+ SLA 3D printer (Formlabs, Somerville, Mass., USA), and were UV cured for 15 minutes using a photochemical reactor (Rayonet, Branford, Conn., USA).

The funnel-guide was formed in agarose by using the negative funnel-guide as a mold. Molten 2% agarose (weight/volume) was added to either a cuvette, or 1 cm inner diameter polycarbonate square plastic tubing (McMaster Carr, Elmhurst, Ill., USA), and the funnel-guide mold inserted. After agarose solidification, the funnel-guide mold was removed, leaving behind a void in the agarose in the shape of the desired funnel-guide. Funnel-guides used for velocity measurements were filled with serum-free media and immediately used. Funnel-guides used for toroid fusion and tube creation were removed from the tubing and equilibrated in 10 mL serum-free media overnight at 37° C. Toroids and honeycombs were added to the funnel-guide using a wide-bore pipette tip.

Measuring the Velocity of Microtissues.

A cuvette (Dynalon Corporation, Rochester, N.Y., USA) filled with serum-free media was used to measure the free fall velocity of HUVEC and HepG2 spheroids, toroids, and HepG2 honeycombs. Endothelial Growth Medium supplemented with 1% penicillin/streptomycin was used for the HUVEC microtissues, and Eagle's Minimum Essential Medium supplemented with 1% penicillin/streptomycin was used for the HepG2 microtissues.

Microtissues were placed into the cuvette using wide-bore 200 µl or 1000 µl pipette tips. The addition of the microtissue and its fall to the bottom of the cuvette was recorded using a DinoLite digital microscope (BigC Dino-Lite, Torrance, Calif., USA) and the ImageJ (National Institutes of Health, Bethesda, Md., USA) Webcam Capture plugin that captured images every 250 msec. Time-lapse images were used to calculate the velocities of falling microtissues in all three chambers.

Evaluation of Funnel-Guides and Tube Extraction.

The inventors assessed microtissue alignment within the stacking chamber by visual inspection and documented the inspection with the DinoLite digital microscope. Images of the side of the stack and the bottom of the stack looking into the lumen were taken at 0 hours and 24 hours.

Microtissue fusion was evaluated via extraction of the tissue tube from the funnel-guide and gentle manipulation with tweezers. Funnel-guides used for tube extraction were cut with a razor blade vertically into two pieces after equilibration. The two halves were then placed into the square polycarbonate tubing, filled with the appropriate culture media and toroids added to create a stack. Stacks were allowed to fuse overnight at 37° C. and 5% $CO_2$. At 24 hours, the tubes created by the fused toroids were extracted by removing the funnel-guide and placing it into a 100 mm Petri dish (Corning Incorporated, Corning, N.Y., USA) filled with 40 mL of serum-free media Spatulas were then used to gently lift one half of the funnel-guide away from the other, releasing the tube from the stacking chamber.

Cell Viability Assessments.

Microtissue viability assessments can be performed using the Live/Dead Viability/Cytotoxicity kit (Invitrogen, Carlsbad, Calif., USA). Cells are rinsed with phosphate-buffered saline (PBS) and stained with 2 µM calcein-AM and 4 µM ethidium homodimer-1 (in 300 µl PBS) at 37° C. for 30 min, followed by image acquisition.

For example, for LIVE/DEAD staining, the inventors washed HepG2 toroid microtissues for 10 min in EMEM supplemented with 1% penicillin/streptomycin thrice. Toroids were then incubated in a mixture of EMEM supplemented with 1% penicillin/streptomycin with 1 mm calcein-AM and 4 mm ethidium homodimer-1 (Invitrogen, Carlsbad, Calif., USA) for 1 hour at 37° C. Twenty-four-hour toroids were removed from gels and pipetted into the mixture. Microtissue viability was assessed with fluorescent imaging using a Zeiss Axio Observer Z1 equipped with an AxioCam MRm camera with ZEN software (Carl Zeiss Microscopy, LLC, Thornwood, N.Y., USA) and an X-Cite 120 fluorescence illumination system (EXFO Photonic Solutions, Mississauga, Ontario, Canada).

Statistical Analysis.

Statistical analysis of velocities was done using a Kruskal-Wallis one-way analysis of variance (ANOVA) on ranks, and a post hoc analysis using Dunn's Method, with significant values having a $p<0.05$.

Quality Control.

To control the quality of the toroids those of skill in the tissue engineering art are putting into the funnel-guide, the inventors developed a quality control algorithm. Toroids that are in the wide-bore pipette tip are imaged from the bottom using a proprietary imaging system. A LabVIEW algorithm is used to identify the toroid within the pipette tip by finding circular edges. The circular edges are found by searching within a given region of interest (ROI) and identifying the largest gradient between two concentric rings. First, the algorithm uses the entire image as its region of interest to identify the inner edge of the pipette tip. After the inner edge of the pipette tip is located, the algorithm uses the area of the pipette as the region of interest to identify the outer edge of the toroid. Finally, the algorithm uses the outer edge of the toroid as the region of interest to identify the inner edge, or the lumen, of the toroid. After the toroid has been identified, the toroid can be evaluated using parameters of concentricity and size. This allows those of skill in the tissue engineering art to control the roundness and diameter of toroids that are placed in the funnel-guide, thus increasing probability of alignment.

Example 2

Results

Velocity of Microtissue Sliding Depends on the Angle.

To show that toroids and honeycombs would slide along a non-adherent surface in a liquid environment, the inventors designed a sliding set-up using a goniometer. See, FIG. 1A-D. HepG2 cells were seeded in either toroid ($5 \times 10^4$ per tissue) or honeycomb ($3.75 \times 10^5$) shaped micro-molds. Twenty four hours after self-assembly, toroids and honeycombs were removed from the micro-molds and placed at inclines of 15°, 20° or 30°.

The tissue sliding set-up consisted of a 30 mL beaker sitting in a circular recess of an acrylic platform attached to a goniometer (Thorlabs, Newton, N.J., USA). Beneath the beaker were grid lines for measuring distance. The sliding surface was created by pipetting 3 mL of 2% (weight/volume) molten agarose into a 30 mL beaker, allowing it to solidify and then equilibrating it with 12 mL of room temperature Eagle's Minimum Essential Medium supplemented with 1% penicillin/streptomycin. The beaker was then placed in the acrylic platform at an angle set by the goniometer.

HepG2 toroid and honeycomb microtissues were carefully placed into the beaker mounted on the goniometer using 200 µl or 1000 µl pipette tips (VWR, Radnor, Pa., USA), made to have wider bores by cutting with a sterile razor blade (McMaster Carr, Elmhurst, Ill., USA). Once in the beaker, the time to travel 10 mm was measured for angles of 15°, 20°, and 30° and velocities calculated for toroids and honeycombs.

Toroids and honeycombs slid at all three angles tested, and the velocities of all inclines were significantly different, with microtissues sliding the fastest at 30°. Additionally, velocities of toroids and honeycombs were significantly different, with honeycombs sliding at a faster velocity.

Toroids Spontaneously Right Themselves During Free Fall.

To show that a stack of toroids could be built by sliding, the inventors designed a device molded in agarose. In this forty-first embodiment, the funnel-guide has two components, a funnel chamber (30°, 10 mm) and a stacking chamber (1.5 mm diameter, 20 mm tall). See, FIG. 2A-F. The inventors filled the device with media, dropped in toroids and observed their sliding and settling behavior using real-time video. Toroids settled onto the wall of the device, and slid into the stacking chamber with a vertical orientation, preventing lumen alignment.

Figure 2:
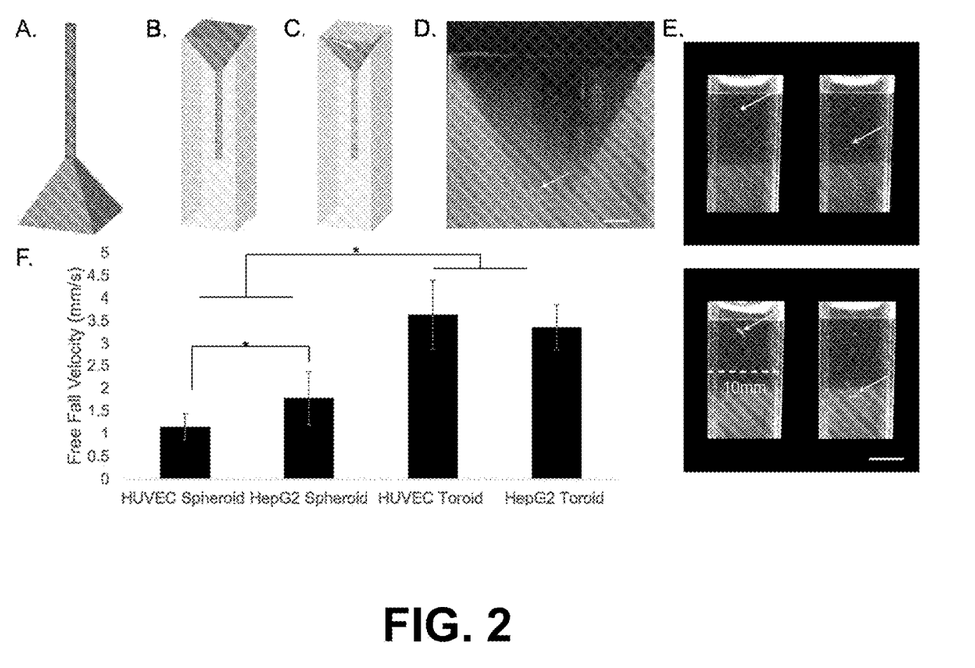
FIG. 2 is a set of figures, images, and charts showing that toroids right themselves to a horizontal orientation when in free fall.

When dropping toroids, the inventors noticed an unexpected behavior. Independent of its initial orientation, a free falling toroid righted itself and assumed a horizontal orientation for the rest of the free fall. Accordingly, the inventors dropped toroids into a cuvette to observe their free fall and calculate their velocity. On average, the toroids required 10 mm of free fall to right themselves and to assume a horizontal orientation.

To show this was not cell type specific, the inventors tested HUVEC toroids which also righted themselves within 10 mm of free fall. The inventors also tested HepG2 and HUVEC spheroids, which fell at a slower velocity than the toroids.

Defining the Critical Mold Components.

To harness the ability of toroids to right themselves, the inventors designed another funnel-guide (FG). See, FIG. 3A-F. In this forty-second embodiment, the funnel-guide had three chambers, a free fall chamber (10 mm in height), a funnel chamber (13 mm in height), and a stacking chamber (10 mm in height). The angle of the funnel was 77°.

To test the performance of the guide, the inventors dropped in toroids and observed their settling behavior and measured their velocity. Surprisingly, unlike our first mold with a 30° funnel, toroids did not settle onto the wall. Instead, they righted themselves and remained horizontal as the funnel guided them down to the stacking chamber. Velocities in the free fall, funnel and stacking chambers were all significantly different. However, the toroids were misaligned when they settled into the circular stacking chamber (50 µm gap between the toroid and the walls).

To improve settling and alignment, in a forty-third embodiment, the inventors changed the funnel and stacking chamber sections to be square, to decrease resistance between the microtissue and the mold wall. Velocities in the free fall and stacking chamber, and funnel and stacking chamber were statistically significant. The square stacking chamber had a 300 µm space on the four corners and a 50 µm gap along the sides and resulted in better alignment. Using the funnel-guide with the square stacking chamber, the inventors created a stack of 45 aligned toroids.

Stacking of Toroids Occurs Independently of Size and Cell Type.

To show that the funnel-guide of the invention can be used with toroids of different sizes and cell types, the inventors tested large HepG2 toroids (diameter of 2.2 mm, $1.2 \times 10^5$ cells) and small HUVEC toroids (diameter of 700 µm, $5.0 \times 10^4$ cells). See, FIG. 4A-I. When dropped into the funnel-guide, large HepG2 toroids righted themselves to a horizontal orientation and were guided by the funnel into the stacking chamber (2.3 mm diameter, square in shape) to form a stack of 20 toroids. When dropped into the funnel-guide, smaller HUVEC toroids were also guided into the stacking chamber (800 µm diameter, square in shape) and formed a stack of 20 toroids. The stacks were incubated for 24 hours at 37° C. Images before and after incubation showed that the toroids had fused into a tube. This fusion was confirmed by extracting the tubes from the gels.

Stacking Honeycombs.

To show that honeycombs (3.4 mm longest diameter, $3.75 \times 10^5$ HepG2 cells) can be stacked, the inventors measured the honeycombs' velocity in free fall. They observed that honeycombs also righted themselves. See, FIG. 5A-E. The inventors fabricated a funnel-guide for honeycombs.

The inventors tested the honeycomb funnel-guide by dropping in 10 honeycombs. The honeycombs righted themselves and were guided down to the stacking chamber (3.5 mm in diameter, honeycomb-shaped) to form an aligned stack of 10 honeycombs. The velocities in each chamber were significantly different. Imaging from the bottom of the stack showed that all seven lumens were aligned.

Example 3

Funnel-Guided Positioning of Multi-Cellular Microtissues to Build Macrotissues

The inventors fabricated a funnel to guide falling toroids and honeycombs into precise positions and stack them wherein they fused to form tubular structures. The inventors tested several cell types and toroid sizes. In a forty-fourth embodiment, using the funnel-guide, the inventors created a stack of 45 toroids that fused into a tube 5 mm long with an inner diameter of 600 µm.

Example 4

Automation and Quality Control of the Process for Building Macrotissues

The inventors automated the process of building tubes. Automation is used not only for removing a stack of toroids from the funnel guide, but also placing an individual toroid onto the funnel guide. In a forty-fifth embodiment, the invention provides the automation for picking up toroid, QC/QA step and then deposit in funnel guide.

The inventors formed toroids in a 96-well dish, one toroid per well and used a liquid handling robot with a pipettor to pick up a toroid from a well and then move over an upward-facing camera that takes a picture of the toroid inside the pipette. The toroid settles to the bottom of the liquid held by the pipette such that the upward facing camera can take a picture of it.

At this QC/QA step, where the toroid can be visualized before depositing into the funnel guide, the inventors are building an image-analysis step that assesses whether or not a building part has the proper specifications (e.g., intact toroid, size, thickness, etc.) for addition to the funnel guide. Those parts that don't meet the specifications set by those of skill in the tissue engineering art are rejected.

Figure 6:
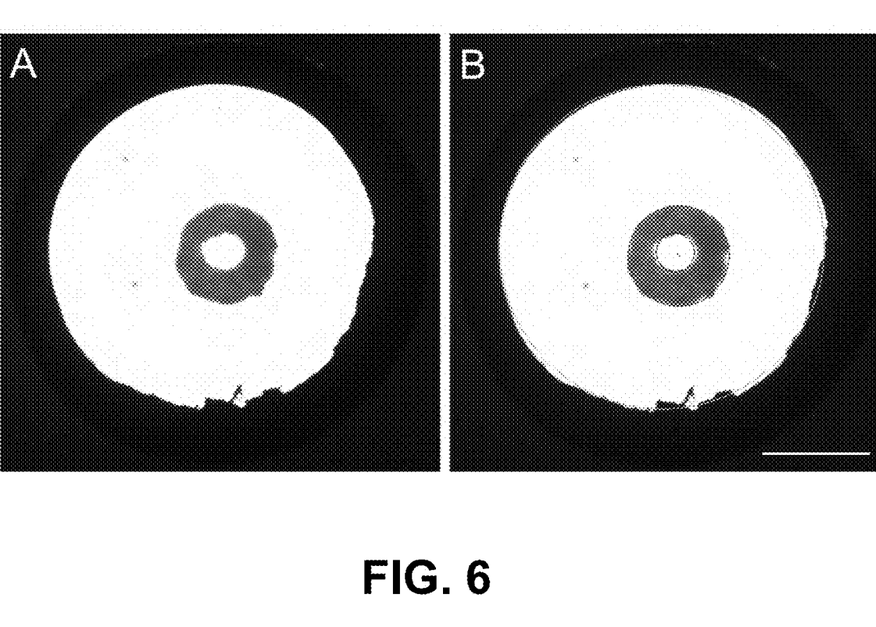
FIG. 6 is a pair of figures showing toroid quality control.

FIG. 6 is a picture of a toroid from our upward facing camera.

OTHER EMBODIMENTS

The foregoing description is illustrative of particular aspects of the invention but is not meant to be a limitation upon the practice thereof.

Various modifications of the present invention, in addition to those shown and described herein, will be apparent to those skilled in the tissue engineering art of the above description. Such modifications are also intended to fall within the scope of the appended claims.

All reagents are obtainable from commercial sources known in the tissue engineering art unless otherwise specified.

Patents, publications, and applications mentioned in the specification are indicative of the levels of those skilled in the art to which the invention pertains. These patents, publications, and applications are incorporated herein by reference to the same extent as if each patent, publication, or application was specifically and individually incorporated herein by reference.

The foregoing description of particular aspects is merely exemplary and is in no way intended to limit the scope of the invention, its application, or uses, which may, of course, vary. The invention is described in relation to the non-limiting definitions and terminology included herein. These definitions and terminology are not designed to function as a limitation on the scope or practice of the invention but are presented for illustrative and descriptive purposes only. While the compositions or processes are described as using specific materials or order of individual steps, it is appreciated that materials or steps may be interchangeable such that the description of the invention may include multiple parts or steps arranged in many ways as is readily appreciated by one of skill in the tissue engineering art.

The terminology used herein is for describing particular aspect only and is not intended to be limiting. As used herein, the singular forms "a," "an," and "the" are intended to include the plural forms, including "at least one," unless the context indicates otherwise. Or means "and/or." As used herein, the term "and/or" includes any combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, a reference to values stated in ranges includes every value within that range.

Unless otherwise defined, all terms (including technical and scientific terms) used herein have the same meaning as commonly understood by one of ordinary skill in the tissue engineering art. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Having thus described in detail preferred embodiments of the present invention, other embodiments will be evident to those of ordinary skill in the tissue engineering art. It should be understood that the foregoing detailed description is provided for clarity only and is merely exemplary. The spirit and scope of the present invention are not limited to the above examples but are encompassed by the following claims.

What is claimed:

1. A device for assembling multi-cellular structures constructed from stacked microtissues, wherein the microtissues have the shape of a toroid, wherein the multi-cellular structures are stacked in a manner to cause openings defined by the multi-cellular structures to substantially align, the device comprising a funnel-guide, the funnel-guide comprising:
   (a) a free-fall chamber,
   (b) a funnel chamber, comprising a funnel with an angle between $30 < \measuredangle < 77$, and
   (c) a stacking chamber, wherein the stacking chamber is square-shaped and has a width and diagonal slightly larger than a toroid diameter,
   such that in the operation of the device,
   (i) the toroids spontaneously right themselves during free fall to align with openings defined by the multi-cellular structures in the stacking chamber,
   (ii) causing the multi-cellular structures in the stacking chamber to be stacked in a manner to cause openings defined by the multi-cellular structures to substantially align,
   (iii) such that the stacked microtissues comprise a lumen.

2. The device of claim 1, wherein the free-fall chamber is at least 10 mm in height.

3. The device of claim 1, wherein the stacking chamber has a square shape.

4. The device of claim 1, wherein the stacking chamber is honeycomb-shaped.

5. The device of claim 1, wherein the stacked microtissues comprising a lumen comprises a stack of at least twenty-five toroids.

6. A device for assembling multi-cellular structures constructed from stacked microtissues, wherein the microtissues have the shape of a honeycomb, wherein the multi-cellular structures are stacked in a manner to cause openings defined by the multi-cellular structures to substantially align, the device comprising a funnel-guide, the funnel-guide comprising:
   (a) a free-fall chamber,
   (b) a funnel chamber, comprising a funnel with an angle between $30 < \measuredangle < 77$, and
   (c) a stacking chamber,
   such that in the operation of the device,
   (i) the honeycombs spontaneously right themselves during free fall to align with openings defined by the multi-cellular structures in the stacking chamber,
   (ii) causing the multi-cellular structures in the stacking chamber to be stacked in a manner to cause openings defined by the multi-cellular structures to substantially align,
   (iii) such that the stacked microtissues comprise lumens.

7. The device of claim 6, wherein the stacked microtissues comprising a lumen comprises a stack of at least five honeycombs.

* * * * *